United States Patent [19]
Nishihira et al.

[11] Patent Number: 5,869,729
[45] Date of Patent: Feb. 9, 1999

[54] METHOD OF PRODUCING AN ESTER COMPOUND

[75] Inventors: Keigo Nishihira; Shuji Tanaka; Yuki Nishida; Noriaki Manada; Toshio Kurafuji; Masato Murakami, all of Ube, Japan

[73] Assignee: Ube Industries, Ltd., Ube, Japan

[21] Appl. No.: 670,552

[22] Filed: Jun. 27, 1996

Related U.S. Application Data

[63] Continuation-in-part of Ser. No. 245,415, May 18, 1994, abandoned.

[30] Foreign Application Priority Data

May 21, 1993 [JP] Japan ................................ 5-119870
May 21, 1993 [JP] Japan ................................ 5-119871

[51] Int. Cl.$^6$ .................................................. C07C 69/96
[52] U.S. Cl. ...................... 558/277; 560/191; 560/204; 558/280
[58] Field of Search ............................ 558/277, 280; 560/204

[56] References Cited

U.S. PATENT DOCUMENTS 4,260,810  4/1981  Umemura et al. .
4,714,785  12/1987  Manner .
4,814,524  3/1989  Briody et al. .
5,162,563  11/1992  Nishihira et al. .
5,214,184  5/1993  Matuzaki et al. .
5,214,185  5/1993  Nishihira et al. .

FOREIGN PATENT DOCUMENTS 0425197  5/1991  European Pat. Off. .
2545659  4/1977  Germany .

OTHER PUBLICATIONS

Acid–Catalyzed Decomposition of Chlor–and Fluoroformates, Nakanishi, et al, pp. 5033 and 5034.

*Primary Examiner*—Samuel Barts
*Attorney, Agent, or Firm*—Burgess, Ryan & Wayne

[57] ABSTRACT

An ester compound, for example, carbonic acid ester or succinic acid ester, is produced by catalytically reacting, in gas phase, carbon monoxide with a nitrous acid ester and optionally an olefin in the presence of a catalyst and in the presence of a chlorine-containing substance, bringing the reaction product-containing mixed gas into contact with a solid catalyst such as activated carbon or inorganic oxide to reduce the content of the chlorine-containing substance, cool-condensing the resultant mixed gas, and collecting the target ester compound from the condensed liquid.

15 Claims, No Drawings

METHOD OF PRODUCING AN ESTER COMPOUND

CROSS REFERENCE TO RELATED APPLICATION

This application is a continuation-in-part application of prior U.S. patent application Ser. No. 08/245,415, filed on May 18, 1994, now abandoned.

BACKGROUND OF THE INVENTION

1. Field of the Invention

The present invention relates to a method of producing an ester compound.

More particularly, the present invention relates to a method of producing an ester compound, in which method a chloroformic acid alkyl ester is decomposed into a corresponding alkyl chloride and simultaneously a content of hydrogen chloride or chlorine is reduced. The method of the present invention is useful to produce an ester compound and refine various mixed gases containing a chloroformic acid alkyl ester and hydrogen chloride or chlorine in various concentrations, by bringing the chloroformic acid alkyl ester-containing gas into contact with a specific catalyst and thereby converting the chloroformic acid alkyl ester to an alkyl chloride, and simultuneously reducing the content of hydrogen chloride or chlorine and removing the alkyl chloride from the mixed gas.

The method of-the present invention is applicable to production of a mixed gas from a gas phase catalytic carbonylation reaction of carbon monoxide with at least a nitrous acid ester in the presence of a solid catalyst and a chlorine-containing substance, and containing, as a by-product, a chloroformic acid alkyl ester in addition to the resultant carbonylation product, for example, dialkyl carbonate or dialkyl succinate. The method of the present invention can contribute to preventing corrosion in a refining apparatus due to the chloroformic acid alkyl ester contained in the gas mixture.

2. Description of Related Art

As a known method of decomposing a chloroformic acid ester J. Am. Chem. Soc., 77, 5033 (1955) discloses a method of converting a chloroformic acid ester to an alkyl chloride by heating the chloroformic acid ester in the presence of a Lewis acid such as boron trifluoride. This method is disadvantageous in that a long time is necessary for the decomposition of a lower alcohol ester of chloroformic acid and the resultant degree of decomposition is low.

Also, German Unexamined Patent Publication (DE-OS) No. 2,545,659 discloses a method of producing an alkyl chloride by heating a chloroformic acid ester at a temperature of 120° to 130° C. in an aprotic solvent, for example, N-methylpyrrolidone. This method is disadvantageous in that this is a liquid phase method in which a special solvent must be employed and a solvent vessel must be provided, and thus is not economical for industrially decomposing the chloroformic acid ester.

U.S. Pat. No. 4,260,810 and U.S. Pat. No. 5,162,563 disclose that in catalytic carbonylation reactions, for example, in carbonic acid ester-synthesis reactions or dicarboxylic acid diester-synthesis reactions, of carbon monoxide with at least nitrous acid esters in a gas phase in the presence of a solid catalyst comprising a platinum group metal chloride carried on a carrier, the catalytic activity of the solid catalyst gradually decreases during the reaction, and in the industrial procedure, a small amount of a chlorine-containing substance, for example, hydrogen chloride, chlorine or a chloroformic acid ester, is continuously fed into the reaction system to prolong the durability of the catalyst and to maintain its selectivity for the targeted compound at a desired level or to enhance its selectivity.

In the above-mentioned carbonylation reaction procedures, the resultant reaction product mixture produced in the reaction system contains a small amount of a chloroformic acid alkyl ester derived from hydrogen chloride or chlorine added to the reaction system or a small amount of a chloroformic acid alkyl ester, hydrogen chloride or chlorine added to the reaction system, in addition to the aimed reaction product, for example, a carbonic acid ester or dicarboxylic acid diester, non-reacted fractions of carbon monoxide and nitrous acid ester, and another additive, for example, nitrogen monoxide and nitrogen, and therefore, the chloroformic acid alkyl ester and hydrogen chloride or chlorine is brought together with the targeted ester compound into a collecting and refining process for the targeted ester compound. Where the chloroformic acid alkyl ester, which has a poor resistance to hydrolysis or alcoholysis, is introduced into the collecting and refining process, the chloroformic acid alkyl ester is decomposed to a corresponding corrosive chlorine-containing substance, for example, hydrogen chloride, and the corrosive chlorine-containing substance contaminates the targeted product and corrodes the apparatus. Therefore, in this case, it is required to further refine the product to remove the corrosive chlorine-containing substance, or to make the refining process apparatus by a specific material having a high resistance to the corrosive chlorine-containing substance. Namely, the corrosive chlorine-containing substance contained in an industrial product causes significant disadvantages in cost and/or production efficiency.

Nevertheless, with respect to the carbonylation reaction product containing a small amount of a chloroformic acid alkyl ester, it has, until now, not been known how to decompose it to a substantially non-corrosive substance with a high economical efficiency.

Accordingly, there is a strong demand for a method of decomposing chloroformic acid alkyl esters to a substantially non-corrosive substance and reducing the content of corrosive chlorine-containing substance efficiently and economically, which method is useful, for example, for refining a reaction product mixture derived from carbonylation reactions of carbon monoxide with at least a nitrous acid ester.

SUMMARY OF THE INVENTION

An object of the present invention is to provide a method of producing an ester compound at high efficiency and low cost, which method enables corrosive chlorine-containing substances contained in the reaction product-containing mixed gas to be decreased in content thereof, and thus the target product to have a high quality, and the reaction apparatus to be prevented from corrosion.

Another object of the present invention is to provide a method of producing an ester compound by a carbonylation reaction of carbon monoxide with a reactant comprising a nitrous acid ester, which method comprises a specific step of bringing the reaction product-containing mixed gas into contact with a specific solid catalyst, to decrease the content of corrosive chlorine-containing substances contained in the mixed gas.

A further object of the present invention is to provide a method of producing an ester compound by a carbonylation reaction of carbon monoxide with a reactant comprising a nitrous acid ester, in the presence of a catalyst and in the presence of a chlorine-containing substance, in an enhanced quality at a high efficiency, while decomposing the corrosive chloroformic acid alkyl ester and reducing the content of the corrosive hydrogen chloride or chlorine in the resultant reaction product-containing mixed gas, to prevent corrosion of the reaction apparatus.

The above-mentioned objects can be attained by the method of the present invention of producing an ester compound which comprises:

(1) catalytically reacting, in a gas phase, carbon monoxide with a reactant comprising a nitrous acid ester in the presence of a carbonylation reaction catalyst and in the presence of chlorine-containing substance, to prepare a reaction product-containing mixed gas containing resultant ester compound and a corrosive chlorine-containing substance;

(2) bringing the reaction product-containing mixed gas into contact with a solid catalyst comprising at least one member selected from the group consisting of activated carbon and inorganic oxides, to reduce the content of the corrosive chlorine-containing substance in the reaction product-containing mixed gas of step (1).

(3) cool-condensing the resultant reaction product-containing mixed gas of step (2); and (4) collecting the resulting ester compound from the cool-condensed liquid of step (3).

An embodiment of the method of the present invention comprises the steps of:

(A) catalytically reacting, in gas phase, carbon monoxide with a reactant comprising a nitrous acid ester, in the presence of a carbonylation reaction catalyst and in the presence of hydrogen chloride, to produce a reaction product-containing mixed gas containing resultant ester compound, hydrogen chloride and chloroformic acid alkyl ester, and (B) bringing the reaction product-containing mixed gas of step (A) into contact with a solid catalyst comprising at least one member selected from activated carbon and inorganic oxides, to decompose the chloroformic acid alkyl ester and simultaneously reduce the content of hydrogen chloride in the reaction product-containing mixed gas of step (A).

(C) cool-condensing the resultant reaction product-containing mixed gas of step (B); and (D) cooling the ester compound from the cool-condensed liquid of step (C).

The gas phase catalytic carbonylation reaction may be a carbonic acid ester-synthesis reaction, a dicarboxylic acid diester-synthesis reaction or a succinic acid diester synthesis reaction.

Usually, the chlorine-containing substance comprises at least one member selected from the group consisting of chlorine, hydrogen chloride and chloroformic acid alkyl esters.

Preferably, the chloroformic acid alkyl ester is a reaction product mixture derived from a gas phase carbonic acid eater-synthesis reaction and the chlorine-containing substance is hydrogen chloride.

In the method of the present invention, it is important that after the catalytic carbonylation reaction step, the resultant ester compound-containing mixed gas is brought into contact with a specific solid catalyst, to reduce a content of the corrosive chlorine-containing substance contained in the mixed gas. In this step, a chloroformic acid alkyl ester which is corrosive to the reaction apparatus is decomposed into a corresponding non-corrosive alkyl chloride, and the content of the corrosive hydrogen chloride or chlorine is significantly reduced.

DESCRIPTION OF THE PREFERRED EMBODIMENTS

In the method of the present invention for producing an ester compound, carbon monoxide catalytically reacts with a reactant comprising a nitrous acid ester and optionally an olefine, in a gas phase, in the presence of a solid carbonylation catalyst and in the presence of a chlorine-containing substance, for example, hydrogen chloride, chlorine or chloroformic acid ester. The gas phase catalytic carbonylation reaction may be a carbonic acid ester synthesis reaction or a dicarboxylic acid diester synthesis reaction disclosed, for example, in U.S. Pat. Nos. 4,260,810, and 5,162,563. The carbonylation reaction product mixture contains a corrosive chlorine-containing substance comprising, for example, a chloroformic acid alkyl ester and hydrogen chloride or chlorine. The chloroformic acid alkyl ester is usually selected from chloroformic acid esters of monohydric lower alkyl alcohols having 1 to 4 carbon atoms, for example, methyl chloroformate, ethyl chloroformate, n- and iso-propyl chloroformates and n-, iso-, and sec-butyl chloroformates. By the method of the present invention, the lower alkyl chloroformate in the reaction product mixture gas is converted to a corresponding lower alkyl chloride, for example, methyl chloride, ethyl chloride, n- or iso-propyl chloride or n-, iso-, or sec-butyl chloride.

The catalytic carbonylation reaction for producing an ester compound from carbon monoxide and a nitrous acid ester can be easily carried out in gas phase by the procedures as disclosed in, for example, U.S. Pat. No. 4,260,810, and U.S. Pat. No. 5,162,563. The products of the carbonylation reaction include carbonic acid esters, for example, dimethyl carbonate and diethyl carbonate; and dicarboxylic acid diesters, for example, dimethyl succinate and diethyl succinate.

The carbonic acid esters can be produced from carbon monoxide and a nitrous acid ester by the following catalytic carbonylation procedures.

The nitrous acid esters usable for the carbonic acid ester production include esters of nitrous acid with lower monohydric aliphatic alcohols having 1 to 4 carbon atoms, particularly, for example, methyl nitrite, ethyl nitrite, n-, and iso-propyl nitrites and n-, iso- and sec- butyl nitrites. In this carbonylation method, a chloroformic acid alkyl ester produced as a by-product and corresponding to the nitrous acid ester employed is contained in the resultant reaction product mixture.

The carbonylation reaction for producing the carbonic acid ester is carried out in the presence of a solid catalyst. This solid catalyst preferably comprises a catalytic metal component comprising at least one member selected from chlorides of platinum group metals, for example, palladium, platinum, iridium, ruthenium and rhodium, and optionally at least one member selected from compounds of iron, copper, bismuth, cobalt, nickel and tin, and a carrier comprising at least one member selected from activated carbon, alumina, diatomaceous earth, silicon carbide and titanium, the catalytic metal component being carried on the carrier.

The chlorides of the platinum group metals include particularly palladium chloride, platinum chloride, iridium chloride, ruthenium chloride and rhodium chloride. Among them, palladium chloride, ruthenium chloride and rhodium chloride are preferably used and palladium chloride is most preferably used for the carbonylation reaction. The amount of the platinum group metal chloride carried on the carrier is preferably 0.1 to 10% by weight, more preferably 0.5 to 2% by weight, in terms of the metal based on the weight of the carrier.

In the catalytic component for the carbonylation reaction, the platinum group metal compounds are not limited to the above-mentioned chlorides, and can be selected from platinum group metals and compounds thereof which are capable of being converted, in the presence of hydrogen chloride, to the above-mentioned chlorides or chloride complexes capable of releasing therefrom chlorine which contributes to the carbonylation reaction.

The platinum group metal compounds include halides, for example, bromides, iodides and fluorides, inorganic acid salts, for example, nitrates, sulfates and phosphates, and organic acid salts, for example, acetates, oxalates and benzoates, of the platinum group metals. Particularly, the platinum group metal compounds are preferably selected from palladium bromide, palladium iodides, palladium fluorides, palladium nitrate, palladium sulfate, palladium phosphates, palladium oxalate and palladium benzoate.

The compounds of the metal group consisting of iron, copper, bismuth, cobalt, nickel and tin, usable for the carbonylation catalyst include halides, for example, chlorides, bromides, iodides and fluorides, inorganic acid salts, for example, nitrates, sulfates and phosphates, and organic acid salts, for example, acetates, of the above-mentioned metals. Preferably, the halides of the above-mentioned metals are employed. The metal compounds are contained preferably in an amount, in terms of the metal, of 1 to 50 gram atom equivalent, more preferably 1 to 10 gram atom equivalent, per gram atom equivalent of the platinum group metal.

When the carbonylation reaction system contains hydrogen chloride, as a chlorine-containing substance, preferably the hydrogen chloride is anhydrous and added in an amount of 1 to 50 molar %, more preferably 5 to 20 molar % based on the molar amount of the platinum group metal contained in the solid catalyst, per hour. For example, when the carbonylation reaction is carried out in a fixed bed reactor at a gas hour space velocity (GHSV) of 3000 $hr^{-1}$, preferably the feed material gas containing 10 to 500 ppm by volume, more preferably 20 to 100 ppm by volume of hydrogen chloride is continuously fed to the solid catalyst-placed reactor.

Also, as a chlorine-containing substance, chlorine or a chloroformic acid ester is fed to the carbonylation reaction system. In this case, the feed material gas, which usually contains 1% by volume or less, preferably 10 to 10,000 ppm by volume, more preferably 20 to 1,000 ppm by volume, of chloroformic acid alkyl ester or 10 to 1,000 ppm by volume, preferably 20 to 500 ppm by volume, of chlorine, is fed to the carbonylation reaction system, to produce the target carbonic acid ester.

In the feed material gas for the carbonylation reaction, preferably carbon monoxide and the nitrous acid ester are diluted with an inert gas and then supplied to the reactor. There is no limitation to the composition of the feed material gas, Usually, for safety, the concentration of the nitrous acid ester is restricted to 20% by volume or less, more preferably 5 to 20% by volume, and for economy, the concentration of carbon monoxide is limited to 5 to 20% by volume. The molar ratio of carbon monoxide to the nitrous acid ester in the feed material gas is preferably 0.1:1 to 10:1, more preferably 0.25:1 to 1:1. Additionally, the material gas is preferably fed into the reactor at a gas hourly space velocity (GHSV) of 500 to 20,000 $hr^{-1}$, more preferably 2,000 to 10,000 $hr^{-1}$.

The carbonylation reaction for producing an ester compound, for example, dimethyl carbonate is usually carried out under mild conditions, for example, at a temperature of from 0° C. to 200° C., more preferably from 50° C. to 120° C. under ambient atmospheric pressure. Of course, the carbonylation reaction can be carried out under an increased pressure, for example, 1 to 20 kg/cm²G, at a temperature of 50° C. to 150° C.

The carbonylation reaction is preferably carried out continuously in a gas phase. The solid catalyst in the reactor may be in the state of a solid bed or a fluidized bed, and preferably in the form of grains having a mesh size of 4 to 200 or fine particles having a particle size of 20 to 100 $\mu$m.

U.S. Pat. No. 5,162,563 discloses an embodiment of the synthesis of dimethyl carbonate. In this synthesis, solid catalyst grains comprising a carrier consisting of activated carbon grains and a catalytic metal component consisting of palladium chloride and bismuth chloride are placed in a gas phase reactor tube, and a feed material gas comprising 15% by volume of methyl nitrite, 10% by volume of carbon monoxide, 3% by volume of nitrogen monoxide, 6% by volume of methyl alcohol, 100 ppm by volume of hydrogen chloride and about 66% by volume of nitrogen, is fed into the gas phase reactor at a temperature of 100° C. under the ambient atmospheric pressure at a gas hourly space velocity (GHSV) of 3000 $hr^{-1}$.

The dicarboxylic acid diester can be produced from carbon monoxide, olefin and nitrous acid ester by the following catalytic carbonylation reaction.

The nitrous acid esters usable for the dicarboxylic acid diester production are the same as those usable for the carbonic acid ester production.

The olefins usable for the dicarboxylic acid diester production include alkenes having 2 to 20 carbon atoms, for example, ethylene, propylene, butene, pentene, hexene, heptene, octene, nonene, decene, cyclopentene, cyclohexene, cycloheptene, cyclooctene and isomers thereof.

The carbonylation reaction for producing the dicarboxyic acid diester is carried out in the presence of a solid catalyst. This solid catalyst comprises a catalytic metal component comprising palladium chloride, and optionally at least one member selected from halides of copper, alkali metals and alkaline earth metals, and the same carrier as usable for the carbonic acid ester production.

The catalytic component for the carbonylation reaction is not limited to palladium chloride, and may be selected from palladium metal and palladium compounds which are capable of being converted, in the presence of hydrogen chloride, to palladium chloride or chloride complexes, and the same as those usable for the carbonic acid ester production.

The amount of palladium chloride carried on the carrier is 0.01 to 10% by weight, preferably 0.5 to 2% by weight in terms of palladium metal, based on the weight of the carrier.

The amount of the other halides than palladium chloride carried on the carrier is 0.1 to 10 gram atom equivalent, preferably 0.5 to 5 gram atom equivalent, in terms of the metal, per gram atom equivalent of the palladium metal.

Also, the carbonylation reaction system may contain hydrogen chloride as a chlorine-containing substance.

Hydrogen chloride is usually added in an amount of 10 to 10,000 ppm by volume, preferably 20 to 2,000 ppm by volume to the feed material gas.

In the feed material gas for the carbonylation reaction, carbon monoxide and nitrous acid ester are diluted with an inert gas and then supplied to the reactor in the same manner as in the carbonic acid ester production. The concentration of carbon monoxide and the molar ratio of carbon monoxide to the nitrous acid ester in the feed material gas are the same as those in the carbonic acid ester production. The olefin is added usually in an amount of 0.1 to 20% by volume, preferably 0.5 to 10% by volume to the feed material gas.

Other parameters for the carbonylation reaction, for example, the gas hourly space velocity (GHSV), temperature, pressure, reaction phase and the state of the solid catalyst are the same as those in the carbonic acid production.

A process for producing a dicarboxylic acid diester, for example, dimethyl succinate is disclosed in, for example, U.S. Pat. No. 5,162,563. In this process, a gas phase reactor tube is packed with solid catalyst consisting of silica beads (carrier) and metallic palladium and copper (II) chloride carried on the beads, and a mixed gas comprising 20% by volume of ethylene, 22% by volume of carbon monoxide, 5% by volume of nitrogen dioxide, and 30% by volume of oxygen is fed to the gas phase reactor tube at a temperature of 145° C. under the ambient atmospheric pressure, at a feeding rate of 700 ml/min, and separately methyl alcohol and 36% by weight hydrochloric acid are vaporized and fed into the reactor at feed rates of 40 ml/min and 0.5 to 2 ml/min, respectively. The gas hourly space velocity (GHSV) of all the material gas is 2500 hr⁻.

In the catalytic carbonylation reaction of carbon monoxide with the nitrous acid ester in the presence of a solid catalyst, and in the additional presence of a chlorine-containing substance such as chlorine, hydrogen chloride or a chloroformic acid ester, for the production of carbonic acid ester, for example, dimethyl carbonate or dicarboxylic acid ester, for example, dimethyl succinate, the resultant carbonylation product mixture gas contains, in addition to the targeted ester compound, non-reacted carbon monoxide and nitrous acid ester, and others, for example, nitrogen monoxide, carbon dioxide, an inert gas and a chloroformic acid ester and hydrogen chloride or chlorine. This carbonylation product mixture gas is fed to the decomposition step of the present invention in which the gas is brought into contact with the decomposition solid catalyst. In this decomposition step, the chloroformic acid ester is selectively decomposed, without affecting the targeted carbonylation product. This decomposition step for the chloroformic acid alkyl ester simultaneously and effectively contributes to reducing the content of hydrogen chloride in the carbonylation product mixture gas.

In the method of the present invention, the gas containing the carbonylation product and the corrosive chlorine-containing substance, for example, a chloroformic acid alkyl ester, is brought into contact with a solid catalyst consisting of at least one member selected from activated carbon and inorganic oxides, to convert the chloroformic acid ester to a corresponding alkyl chloride.

The chloroformic acid alkyl ester to which the method of the present invention is applicable is usually a lower alkyl chloroformate of which the alkyl group preferably has 1 to 4 carbon atoms. The lower alkyl chloroformate is selected from methyl chloroformate, ethyl chloroformate, n and iso-propyl chloroformates, n-, iso- and sec-butyl chloroformates. Namely, the alkyl group of the lower alkyl chloroformate is preferably selected from methyl, ethyl, n-propyl, iso-propyl, n-butyl, iso-butyl, and sec-butyl groups.

In the carbonylation reaction product-containing mixed gas, the concentration of the chloroformic acid alkyl ester is not limited to a specific range thereof. For example, the chloroformic acid alkyl ester concentration is variable through a wide range of from 10 ppm to 10,000 ppm by volume.

Especially, the decomposition procedure of the method of the present invention is advantageously applicable to a gaseous mixture containing the chloroformic acid alkyl ester in a low concentration of from 20 to 10,000 ppm, preferably 20 to 5,000 ppm.

In the method of the present invention, the gas substance which can be contained together with the chloroformic acid alkyl ester in the mixed gas to which the method of the present invention is applied, is not restricted to a specific group of substance. For example, the gas substance which can be mixed with the chloroformic acid alkyl ester is an inert gas, for example, nitrogen, or carbon dioxide gas, and/or a reactive gas, for example, carbon monoxide, nitrous acid esters alcohol or oxygen gas.

The alkyl chloride produced from the decomposition of the chloroformic acid alkyl ester is variable depending on the type of the chloroformic acid alkyl ester, and is preferably an alkyl chloride having 1 to 4 carbon atoms, for example, methyl chloride, ethyl chloride, n- or iso-propyl chloride or n-( iso-, or sec-butyl chloride.

In the decomposition step of the present invention, the catalyst comprises at least one member selected from activated carbon and inorganic oxides. The catalyst preferably consists of an activated carbon. There is no limitation to the type, form, size, physical properties, for example, specific surface area and density, and/or chemical properties, for example, acid strength, of the activated carbon, as long as the activated carbon is selected from those usable as a catalyst carrier, an absorbent or decoloring agent. Preferably, the activated carbon used as a catalyst for the method of the present invention has a specific surface area of 10 $m^2/g$ or more, more preferably 100 to 3,000 $m^2/g$, still more preferably 300 to 2,000 $m^2/g$ and is in the form of grains, pellets or honeycombs.

The inorganic oxides usable as a catalyst for the decomposition step of the present invention are not restricted to those having specific form, size, physical properties, for example, specific surface area and density and/or chemical properties, for examples, acid strength. Preferably, the inorganic oxides are in the form of grains, pellets or honeycombs and have a specific surface area of 10 to or $m^2/g$ or more, more preferably 100 to 1,000 $m^2/g$, still more preferably 300 to 800 $m^2/g$.

The inorganic oxides are preferably selected from those usable as a catalyst carrier, for example, various types of aluminas including γ-alumina, α-alumina, and η-alumina, silica-alumina, synthetic zeolites, for example, X, Y and A-type synthetic zeolites and molecular sieves, natural zeolites, for example, natrolite and mordenite, silica, titania and zirconia.

The decomposition catalyst preferably comprises at least one member selected from activated carbon, and aluminum-containing inorganic oxides, for example, γ-alumina, α-alumina, η-alumina and zeolites, in the form of grains.

The decomposition reaction of the chloroformic acid alkyl ester into a corresponding alkyl chloride, in accordance with the present invention can be carried out in a batch type procedure. From an industrial point of view, the decomposition reaction is preferably carried out by a gas phase continuous procedure. In this continuous procedure, the catalyst can be employed in a fixed bed or a fluidized bed.

In the method of the present invention, the decomposition step of the chloroformic acid alkyl ester into a corresponding alkyl chloride is carried out preferably at a gas hourly space velocity (GHSV) of the chloroformic acid ester-containing gas of 500 to 30,000 hr$^{-1}$, more preferably 2,000 to 20,000 hr$^{-1}$, at a decomposition temperature of 0° C. to 220° C., more preferably, 10° C. to 200° C. Still more preferably, the decomposition temperature is maintained at a level ranging from 20° C. to 150° C. In the method of the present invention, the decomposition step may be carried out at the same gas hourly space velocity (GHSV) as that in the carbonylation reaction step.

Since the dependency of the decomposition reaction on pressure is low, the decomposition step can be carried out under a pressure of from ambient atmospheric pressure to an increased pressure for example, from 1 to 20 kg/cm$^2$G, preferably 2 to 5 kg /cm$^2$G, without difficulty.

Where the decomposition reaction does not cause a generation of a large amount of heat, the contact of the chloroformic acid alkyl ester-containing gas with the catalyst can be effected in a multiple tube type reactor or a single tube type reactor in which the catalyst comprising the activated carbon and/or the inorganic oxide is filled. The decomposition reaction may be carried out in another type of reactor.

During the decomposition reaction step; substantially all of the chloroformic acid alkyl ester is converted to a corresponding alkyl chloride. Therefore, when the resultant alkyl chloride-containing gas is fed to a next step, corrosion of conduits and/or apparatus of the next step due to this gas is prevented or significantly reduced.

The method of the present invention is advantageously applied to a reaction product mixture gas derived from a gas phase catalytic carbonylation reaction of carbon monoxide with a nitrous acid ester.

When the carbonylation reaction product-containing mixed gas is subjected to the decomposition step of the present invention, the decomposing catalyst may contain a metal component comprising a platinum group metal which is useful as a catalytically active component for the carbonylation catalyst, in a small amount in which the metal component cannot serve as a catalytic component. Preferably, the amount of the platinum group metal carried on the decomposition catalyst is restricted to a level of less than 0.1% by weight, more preferably 0 to 0.05% by weight based on the weight of the decomposition catalyst. Still more preferably, the platinum group metal is substantially not present in the decomposition catalyst.

The amount of the decomposition catalyst employed in a decomposition step is preferably 2 to 500%, more preferably 5 to 200%, still more preferably 10 to 50%, based on the volume of the carbonylation catalyst used for the carbonylation reaction.

The decomposition catalyst may be placed in the carbonylation reactor at a location close to an outlet of the carbonylation reactor. In this case, the carbonylation reaction and the decomposition reaction can be carried out in one and the same reactor and thus the reaction apparatus is very simple. Also, the decomposition catalyst may be placed in a decomposition reactor connected to the outlet of the carbonylation reactor in which the carbonylation catalyst is placed. For example, as disclosed in U.S. Pat. No. 5,214, 185, the decomposition reactor containing the decomposition catalyst is located in a conduit line between the carbonylation reactor for producing dimethyl carbonate and an absorption column.

In this case, since the amount of heat generated by the decomposition reaction is small, the decomposition reaction can be effected in a multiple tube type reactor, a single tube type reactor or another type of reactor without difficulty.

The feed gas for the decomposition step is the reaction product mixture gas delivered from the carbonylation reaction system and containing a chloroformic acid alkyl ester produced from hydrogen chloride or chlorine added to the carbonylation reaction system. The reaction product mixture gas also contains non-reacted fraction of hydrogen chloride or chlorine added to the carbonylation reaction system, in a concentration of 10 to 10,000 ppm by volume, preferably 20 to 2,000 ppm by volume.

When hydrogen chloride is added to the carbonylation reaction system, the resultant reaction product mixture gas contains chloroformic acid alkyl ester in a low concentration of from 10 to 10,000 ppm by volume, preferably 20 to 2,000 ppm by volume, and hydrogen chloride in a low concentration of from 20% by volume or less, based on the volume of the chloroformic acid alkyl ester present in the reaction product mixture gas.

Accordingly, the reaction product mixture gas to be subjected to the decomposition step of the chloroformic acid alkyl ester contains a targeted carbonylation reaction product, for example, a carbonic acid ester or dicarboxylic acid diester, by-products, for example, oxalic acid diester, and others, for example, carbon monoxide, nitrous acid ester, nitrogen monoxide, carbon dioxide and nitrogen. These substances other than the chloroformic acid alkyl ester contained in the feed gas do not cause any problems for the decomposition reaction of the chloroformic acid ester.

The chlorine-containing substances, for example, hydrogen chloride, chlorine or chloroformic acid alkyl ester, added to the carbonylation reaction system serves as an activating agent for the solid carbonylation catalyst so as to maintain the catalytic activity of the catalyst at a desired high level in the carbonylation step, and then hydrogen chloride or chlorine is converted to a chloroformic acid alkyl ester. By utilizing the decomposition method of the present invention, the chloroformic acid alkyl ester is converted to an alkyl chloride which is not corrosive to the apparatus and can be easily removed from the reaction product mixture.

For example, in a synthesis of dimethyl carbonate as disclosed in U.S. Pat. No. 5,214,185, a decomposition device is located in a portion of a carbonylation reactor or in a portion of a conduit between the carbonylation reactor and an adsorption column, a carbonylation reaction product-containing mixed gas is introduced into the decomposition device to convert methyl chloroformate contained in a small amount in the carbonylation reaction product-containing mixed gas to methyl chloride, and the carbonylation reaction product containing methyl chloride is absorbed and condensed by the absorption column.

The methyl chloride-containing carbonylation reaction product absorbed and condensed in the absorption column is fed to a distill-refining device connected to a bottom outlet of the absorption column. The distill-refining device is, for example, a distillation column or a multistep distillation column. The methyl chloride is discharged from a top outlet of the distill-refining device, and a crude product containing dimethyl carbonate is discharged from a bottom outlet thereof. The crude product has a significantly reduced content of methyl chloride and is subjected to a further refining step.

By the decomposition step for the chloroformic acid alkyl ester, the carbonylation reaction product, namely the targeted carbonic acid ester or dicarboxylic acid diester, is not influenced or converted, and can be supplied to the next step. Also, the content of hydrogen chloride in the carbonylation reaction product-containing mixed gas can be reduced simultaneously with the decomposition of the chloroformic acid alkyl ester. Namely, the decomposition step of the present invention can reduce the content of a hydrogen chloride, and thus is contributory to preventing an undesirable corrosion of apparatus due to the hydrogen chloride.

The resultant carbonylation product-containing mixed gas delivered from the decomposition step is cool-condensed. The targeted carbonylation product is collected from the condensed liquid by a collecting means, for example, distillation. The obtained product has a very small content of the chlorine-containing substance.

EXAMPLES

The present invention will be further explained by the following examples which are merely representative and do not in any way restrict the scope of the present invention.

Example 1

A gas phase glass tube reactor having an inside diameter of 13 mm and a length of 250 mm and equipped with an outside heating jacket was packed with 5 ml of a granular activated carbon having a specific surface area of 1040 m$^2$/g. The inside temperature of the reactor tube was controlled to a level of 120° C. by circulating a heating medium through the outside heating jacket. A mixed gas containing 500 ppm by volume of methyl chloroformate diluted by a nitrogen gas was fed into the reactor tube through a top inlet thereof at a gas hourly space velocity (GHSV) of 4000 hr$^{-1}$, and brought into contact with the decomposition catalyst at a temperature of 120° C. under the ambient atmospheric pressure for one hour, to decompose the methyl chloroformate.

The resultant mixed gas was delivered from the reactor and subjected to a gas chromatographic analysis. It was confirmed that the resultant mixed gas contained no methyl chloroformate and 500 ppm by volume of methyl chloride. Namely, 100% of the methyl chloroformate was decomposed and converted to methyl chloride.

Example 2

The same procedures as in Example 1 were carried out with the following exceptions.

The granular activated carbon was replaced by 1 ml of granular activated alumina having a 24 mesh size.

The concentration of methyl chloroformate was changed to 840 ppm by volume.

The gas hourly space velocity (GHSV) of the mixed gas was changed to 20,000 hr$^{-1}$.

In the resultant mixed gas, no methyl chloroformate was detected, and the concentration of methyl chloride was 840 ppm by volume. It was confirmed that the methyl chloroformate was entirely decomposed.

Example 3

The same procedures as in Example 1 were carried out with the following exceptions.

The granular activated carbon was replaced by 1 ml of granular activated alumina having a 24 mesh size.

The concentration of methyl chloroformate was changed to 800 ppm by volume.

The gas hourly space velocity (GHSV) of the mixed gas was changed to 20,000 hr$^{-1}$. The reaction temperature was changed to 80° C.

In the resultant mixed gas, the concentration of methyl chloroformate was 260 ppm by volume, and the concentration of methyl chloride was 540 ppm by volume. Namely, methyl chloroformate was decomposed at a conversion of 65%.

Example 4

The same procedures as in Example 1 were carried out with the following exceptions.

The granular activated carbon was replaced by 5 ml of granular zeolite available under the trademark of HSZ-320NAD, from Toso.

The concentration of methyl chloroformate was changed to 2400 ppm by volume.

The gas hourly space velocity (GHSV) of the mixed gas was changed to 20,000 hr$^{-1}$.

The resultant mixed gas, contained 430 ppm by volume of methyl chloroformate and 1970 ppm by volume of methyl chloride. Namely, methyl chloroformate was decomposed at a conversion of 82%.

Example 5

The same procedures as in Example 1 were carried out with the following exceptions.

The granular activated carbon was replaced by 10 ml of granular zeolite (HSZ-320NAD, Toso).

The concentration of methyl chloroformate was changed to 2,000 ppm by volume.

The gas hourly space velocity (GHSV) of the mixed gas was changed to 3,000 hr$^{-1}$.

In the resultant mixed gas, no methyl chloroformate was detected, and the concentration of methyl chloride was 2,000 ppm by volume. It was confirmed that methyl chloroformate was entirely decomposed at a conversion of 100%.

Example 6

The same procedures as in Example 1 were carried out with the following exceptions.

The granular activated carbon was replaced by 5 ml granular titania having a 24 mesh size and available under the trademark of DC-3144, from Diamond Catalyst Co.

The concentration of methyl chloroformate was changed to 2,000 ppm by volume.

The gas hourly space velocity (GHSV) of the mixed gas was changed to 6,000 hr$^{-1}$.

The resultant mixed gas contained 800 ppm by volume of methyl chloroformate, and 1,200 ppm by volume of methyl chloride. It was confirmed that methyl chloroformate was decomposed at a conversion of 60%.

Example 7

The same procedures as in Example 1 were carried out with the following exceptions.

The granular activated carbon was replaced by 1 ml of granular γ-alumina available under the trademark of KHA-24, from Sumitomo Kagaku Kogyo K.K.

The concentration of methyl chloroformate was changed to 1,250 ppm by volume.

The gas hourly space velocity (GHSV) of the mixed gas was changed to 20,000 hr$^{-1}$.

13

The resultant mixed gas contained 440 ppm by volume of methyl chloroformate and 810 ppm by volume of methyl chloride. It was confirmed that methyl chloroformate was decomposed at a conversion of 65%.

Example 8

The same procedures as in Example 1 were carried out with the following exceptions.

The granular activated carbon was replaced by 5 ml of granular activated carbon having a specific surface area of 1,300 m$^2$/g.

The concentration of methyl chloroformate was changed to 1,000 ppm by volume.

The gas hourly space velocity (GHSV) of the mixed gas was changed to 6,000 hr$^{-1}$. The decomposition temperature was changed to 40° C.

In the resultant mixed gas, no methyl chloroformate was detected, and the concentration of methyl chloride was 1,000 ppm by volume. It was confirmed that methyl chloroformate was entirely decomposed at a conversion of 100%.

Example 9

The same procedures as in Example 1 were carried out with the following exceptions.

The granular activated carbon was replaced by 5 ml of granular activated carbon having a specific surface area of 490 m$^2$/g.

The concentration of methyl chloroformate was changed to 1,000 ppm by volume.

The gas hourly space velocity (GHSV) of the mixed gas was changed to 6,000 hr$^{-1}$. The reaction temperature was changed to 20° C.

In the resultant mixed gas, no methyl chloroformate was detected, and the concentration of methyl chloride was 1,000 ppm by volume. It was confirmed that methyl chloroformate was entirely decomposed at a conversion of 100%.

Example 10

The same procedures as in Example 1 were carried out with the following exceptions.

The granular activated carbon was replaced by 1 ml of granular activated carbon having a specific surface area of 490 m$^2$/g.

14

The concentration of methyl chloroformate was changed to 2,000 ppm by volume.

The gas hourly space velocity (GHSV) of the mixed gas was changed to 30,000 hr$^{-1}$. The reaction temperature was changed to 40° C.

In the resultant mixed gas, no methyl chloroformate was detected, and the concentration of methyl chloride was 2,000 ppm by volume. It was confirmed that methyl chloroformate was entirely decomposed at a conversion of 100%.

Example 11

The same procedures as in Example 1 were carried out with the following exceptions.

The granular activated carbon was replaced by 1 ml of granular activated carbon having a specific surface area of 490 m$^2$/g.

The concentration of methyl chloroformate was changed to 2,000 ppm by volume.

The gas hourly space velocity (GHSV) of the mixed gas was changed to 30,000 hr$^{-1}$. The reaction temperature was changed to 20° C.

The resultant mixed gas contained 400 ppm by volume of methyl chloroformate and 1,600 ppm by volume of methyl chloride. It was confirmed that methyl chloroformate was decomposed at a conversion of 80%.

Comparative Example 1

The same procedures as in Example 1 were carried out with the following exceptions.

The granular activated carbon was replaced by 10 ml of glass beads available under the trademark of Pilex from Fuji Stone Co.

The concentration of methyl chloroformate was changed to 1,000 ppm by volume.

The gas hourly space velocity (GHSV) of the mixed gas was changed to 3,000 hr$^{-1}$.

The resultant mixed gas contain ed 1,000 ppm by volume of methyl chloroformate, and no methyl chloride was detected. It was confirmed that methyl chloroformate was not decomposed.

The reaction conditions and results of Examples 1 to 11 and Comparative Example 1 are shown in Table 1.

TABLE 1

| Item | Decomposition catalyst | | Decomposition temperature (°C.) | Concentration of methyl chloroformate (ppm by volume) | Gas hourly space velocity (GHSV) (hr$^{-1}$) | Conversion (decomposition percentage) of methyl chloroformate (%) |
|---|---|---|---|---|---|---|
| Example No. | Type | Amount (ml) | | | | |
| Example | | | | | | |
| 1 | Activated carbon(*)$_1$ | 5 | 120 | 500 | 4000 | 100 |
| 2 | Activated alumina | 1 | 120 | 840 | 20000 | 100 |
| 3 | Activated alumina | 1 | 80 | 800 | 20000 | 65 |
| 4 | Zeolite | 5 | 120 | 2400 | 6000 | 82 |
| 5 | Zeolite | 10 | 120 | 2000 | 3000 | 100 |
| 6 | Titania | 5 | 150 | 2000 | 6000 | 60 |
| 7 | Alumina | 1 | 120 | 1250 | 20000 | 65 |

TABLE 1-continued

| Item Example No. | Decomposition catalyst Type | Amount (ml) | Decomposition temperature (°C.) | Concentration of methyl chloroformate (ppm by volume) | Gas hourly space velocity (GHSV) (hr$^{-1}$) | Conversion (decomposition percentage) of methyl chloroformate (%) |
|---|---|---|---|---|---|---|
| 8 | Activated carbon(*)$_2$ | 5 | 40 | 1000 | 6000 | 100 |
| 9 | Activated carbon(*)$_3$ | 5 | 20 | 1000 | 6000 | 100 |
| 10 | Activated carbon(*)$_3$ | 1 | 40 | 2000 | 30000 | 100 |
| 11 | Activated carbon(*)$_3$ | 1 | 20 | 2000 | 30000 | 80 |
| Comparative Example | | | | | | |
| 1 | Glass beads | 10 | 120 | 1000 | 3000 | 0 |

Note:
(*)$_1$ ... Trademark: Shirasagi, made by Takeda Yakuhin K.K.
(*)$_2$ ... Trademark: Kureha Beads, made by Kureha Kagaku K.K.
(*)$_3$ ... Trademark: Molsiebon, made by Takeda Yakuhin K.K.

As mentioned above, in accordance with the method of the present invention, a chloroformic acid ester, for example, alkyl chloroformate, can be easily and econominally decomposed and converted to a corresponding hydrocarbon chloride, for example, alkyl chloride at a high efficiency. Even if the concentration of the chloroformic acid ester in a mixed gas is low, this chloroformic acid ester can be selectively decomposed and converted to the corresponding hydrocarbon chloride at a very high conversion, and can be easily removed from the mixed gas.

Example 12

A stainless steel reactor tube having an inside diameter of 27 mm and a length of 500 mm and equipped with an outside heating jacket was fixed vertically and a bottom portion of the tube was packed with 3.5 ml of granular activated carbon (Shirasagi, Takeda Yakuhin) to form a decomposition reaction layer, and then on the decomposition reaction layer, 25 ml of a solid catalyst consisting of granular activated carbon carrier and a catalytic component consisting of 1% by weight of palladium chloride and 1.2% by weight of copper (II) chloride each in terms of the metal, and carried on the carrier were placed to provide a carbonylation reaction layer.

By circulating a heating medium through the outside heating jacket, the inside temperature of the reactor tube was maintained at 100° C.

Then, a material gas containing 10% by volume of methyl nitrite, 20% by volume of carbon monoxide, 4% by volume of nitrogen monoxide, 8% by volume of methyl alcohol, 50 ppm by volume of hydrogen chloride and the balance consisting of nitrogen gas was fed into the reactor tube through a top inlet of the reactor tube at a flow rate of 100N liters/hr corresponding to a gas hourly space velocity (GHSV) of 28,600 hr$^{-1}$ (based on the decomposition reaction layer) under a reaction pressure of 3 kg/cm$^2$G for 10 hours, to effect a carbonylation and a decomposition. During the reaction procedures, the temperatures of the carbonylation reaction layer and the decomposition reaction layer were maintained at a level of 105° C. to 115° C. and 110° C., respectively, The resultant reaction product mixture gas delivered from the reactor tube was subjected to a gas chromatographic analysis to determine the contents of methyl chloroformate and methyl chloride in the gas mixture.

As a result, no methyl chloroformate was detected, and the concentration of methyl chloride in the delivered gas mixture was 47 ppm by volume.

The carbonylation reaction product was collected by passing the gas mixture through a ice-cooled methyl alcohol bath, and it was subjected to an ion chromatographic analysis. The collected product contained methyl chloroformate and hydrogen chloride, in a total amount of 1 ppm by volume based on the volume of the gas mixture. Also, it was confirmed that dimethyl carbonate was produced at a space time yield (STY) of 380 g/liter·hr and at a selectivity of 88% based on the molar amount of carbon monoxide.

In this example, and Examples 13 and 14 and Comparative Examples 2 and 3, the space time yield (STY) of the targeted carbonylation product such as dimethyl carbonate in g/liter·hr was determined in accordance with the equation (I):

$$\text{STY (g/liter·hr)} = a/(b \times \theta) \qquad (I)$$

wherein θ represents a catalytic reaction time in hours of carbon monoxide with a nitrous acid ester such as methyl nitrite, a represents an amount in grams of the resultant carbonic acid ester such as dimethyl carbonate produced during the catalytic reaction time, and b represents a volume in liters of the carbonylation reaction layer formed in the reactor tube.

Also, in each of Examples 12 to 14 and Comparative Examples 2 and 3, the selectivity in % of the targeted carbonylation product such as dimethyl carbonate was determined based on the molar amount of carbon monoxide supplied to the reaction and in accordance with the equation (II):

$$X(\%) = \{c/(c + 2 \times d + e)\} \times 100 \qquad (II)$$

wherein c, d and e respectively represent molar amounts of the aimed carbonylation product such as dimethyl carbonate, a corresponding oxalic acid diester such as dimethyl oxalate, and carbon dioxide.

Example 13

The same procedures as in Example 12 were carried out with the following exceptions. In the formation of the decomposition reaction layer, 3.5 ml of γ-alumina (available under the trademark of KHA-24, from Sumitomo Kagaku Kogyo K.K.) were packed in place of the granular activated carbon.

The gas mixture delivered from the reactor contained methyl chloroformate in a concentration of 4 ppm by volume and methyl chloride in a concentration of 43 ppm by volume.

After flowing through an ice-cooled methyl alcohol bath, the collected reaction product contained methyl chloroformate and hydrogen chloride in a total amount of 5 ppm by volume in terms of concentration in the gas.

It was confirmed that dimethyl carbonate was produced in a space time yield (STY) of 375 g/liter·hr and at a selectivity of 90% based on the amount of carbon monoxide used.

Comparative Example 2

The same procedures as in Example 12 were carried out with the following exceptions.

No decomposition reaction layer was provided.

The delivered gas from the reactor contained methyl chloroformate in a concentration of 18 ppm by volume, and methyl chloride in a concentration of 27 ppm by volume.

After flowing the delivered gas through an ice-cooled methyl alcohol bath, the collected reaction product contained methyl chloroformate and hydrogen chloride in a total amount of 25 ppm by volume in terms of concentration in the gas.

The dimethyl carbonate was produced in a space time yield (STY) of 377 g/liter·hr and at a selectivity of 88% based on the amount of carbon monoxide used.

Example 14

The same procedures as in Example 12 were carried out with the following exceptions.

In the formation of the decomposition reaction layer, 5 ml of γ-alumina grains (KHA-24) were packed in place of the granular activated carbon, and the carbonylation reaction layer was formed from 25 ml of a catalyst which consisted of a carrier consisting of γ-alumina grains (KHA-24) and a catalytic component consisting of 1.5% by weight of a lithium chloropalladate in terms of palladium, i n accordance with EP-A-0523508 (DE-B-412 3603).

The concentrations of methyl nitrite and hydrogen chloride were changed to 18% by volume and 1,000 ppm by volume, respectively.

The temperatures of the carbonylation reaction layer and the decomposition reaction layer were 108° C. to 120° C. and 114° C., respectively.

After the completion of the reactions, the reaction product was analysed. The gas delivered from the reactor contained 15 ppm by volume of methyl chloroformate and 970 ppm by volume of methyl chloride.

After passing the delivered gas through an ice-cooled methyl alcohol bath, the collected product contained methyl chloroformate and hydrogen chloride in a total amount of 20 ppm by volume in terms of concentration in the gas.

The resultant dimethyl carbonate was obtained in a space time yield of 570 g/liter·hr and at a selectivity of 88% based on the amount of carbon monoxide employed.

Comparative Example 3

The same procedures as in Example 14 were carried out with the following exceptions.

No decomposing reaction layer was formed.

The gas delivered from the reactor contained 537 ppm by volume of methyl chloroformate and 455 ppm of methyl chloride.

After passing the delivered gas through an ice-cooled methyl alcohol bath, the collected product contained methyl chloroformate and hydrogen chloride in a total amount of 550 ppm by volume in terms of concentration in the gas.

The resultant dimethyl carbonate had a space time yield (STY) of 565 g/liter·hr and a selectivity of 88% based on the amount of carbon monoxide employed.

Example 15

The same procedures as in Example 12 were carried out with the exceptions as indicated below.

In the formation of the decomposition reaction layer in the reaction tube, 3 ml of granular γ-alumina (KHA-24) were used in place of the granular activated carbon.

The carbonylation reaction layer was formed from 15 ml of a catalyst for the production of dimethyl succinate. The catalyst consisted of a carrier consisting of the granular γ-alumina (KHA-24) and a catalytic component consisting of 1% by weight of palladium chloride and 1.2% by weight of copper (II) chloride and carried on the carrier.

A material gas consisting of 5% by volume of methyl nitrite, 20% by volume of carbon monoxide, 15% by volume of ethylene, 4% by volume of nitrogen monoxide, 8% by volume of methyl alcohol, 800 ppm by volume of hydrogen chloride and the balance consisting of a nitrogen gas was fed into the reactor at a flow rate of 50 N·liter/hr corresponding to a gas hourly space velocity (GHSV) of 16,700 $hr^{-1}$ based on the decomposition reaction layer. The temperatures of the carbonylation reaction layer and the decomposition reaction layer were 105° C. to 115° C. and 108° C., respectively.

The gas delivered from the reactor was subjected to a gas chromatographic analysis. It was found that the delivered gas contained 10 ppm by volume of methyl chloroformate and 770 ppm by volume of methyl chloride.

After passing the delivered gas through an ice-cooled methyl alcohol bath, the collected reaction product was subjected to an ion chromatographic analysis. It was found that the collected reaction product contained methyl chloroformate and hydrogen chloride in a total amount of 15 ppm by volume in terms of concentration in the gas.

The resultant dimethyl succinate was produced in a space time yield (STY) of 230 g/liter·hr, at a selectivity of 93% based on the amount of carbon monoxide employed.

The space time yield (STY, g/liter·hr) of dimethyl succinate was calculated in accordance with the equation (III):

$$STY \text{ (g/liter·hr)} = f/(b \times \theta') \quad (III)$$

wherein θ' represents a catalytic reaction time in hours of carbon monoxide with ethylene and methyl nitrite, f represents an amount in grams of dimethyl succinate produced during the catalytic reaction time and b represents the volume in liters of the carbonylation reaction layer.

Also the conversion Y of the dimethyl succinate based on the amount of carbon monoxide employed was determined in accordance with the equation (IV):

$$Y(\%) = \{2 \times g/(2 \times g + 2 \times h + i + j)\} \times 100 \quad (IV)$$

wherein g, h, i and j respectively represent molar amounts of the resultant dimethyl succinate, dimethyl oxalate, dimethyl carbonate and carbon dioxide produced during the catalytic reaction time θ' in hours.

The results of Examples 12 to 15 and Comparative Examples 2 and 3 are shown in Table 2.

In Table 2, the concentration $C_1$ in ppm by volume of hydrogen chloride in the reaction product gas delivered from the reactor was calculated in accordance with the equation (V):

$$C_1 = C_2 - C_3 \quad (V)$$

wherein $C_2$ represents a total concentration in ppm by volume of the chlorine-containing substances contained in the reaction product gas delivered from the reactor and $C_3$ represents a concentration in ppm by volume of methyl chloroformate contained in the reaction product gas delivered from the reactor. The concentrations represented by $C_1$, $C_2$ and $C_3$ are based on the volume of the reaction product gas delivered from the reactor.

the presence of a carbonylation reaction catalyst and in the presence of hydrogen chloride, to produce a reaction product-containing mixed gas containing the resultant ester compound, hydrogen chloride and chloroformic acid alkylester in a volume amount of 10 to 10,000 ppm and hydrogen chloride in an amount corresponding to 20% by volume or less of the volume amount of the chloroformic acid alkyl ester;

(B) bringing the reaction product-containing the mixed gas of step (A) into contact with a solid catalyst comprising at least one member selected from the group consisting of activated carbon and inorganic oxides, to decompose the chloroformic acid alkyl ester and simultaneously reduce the content of hydrogen chloride in the reaction product-containing mixed gas of step (A);

(C) cool-condensing the resultant reaction product-containing mixed gas of step (B); and (D) collecting the ester compound from the cool-condensed liquid of step (C).

TABLE 2

| Item Example No. | HCl content in material gas for corbonylation reaction (ppm) | Decomposition catalyst Type | Amount (ml) | Decomposition temperature (°C.) | Methyl chloroformate content ($C_3$) by volume in reaction product gas delivered from reactor (ppm) | $CH_3Cl$ content in gas delivered from reactor (ppm) | Chlorine compound content ($C_2$) by volume in reaction product gas (ppm) | HCl content ($C_1$) by volume in reaction product gas (ppm) | Aimed ester compound (dimethyl carbonate or succinate) Space time yield (STY) (g/l · hr) | Selectivity (%) |
|---|---|---|---|---|---|---|---|---|---|---|
| Example | | | | | | | | | | |
| 12 | 50 | Activated carbon | 3.5 | 110 | 0 | 47 | 1 | 1 | 380 | 88 |
| 13 | 50 | γ-alumina | 3.5 | 110 | 4 | 43 | 5 | 1 | 375 | 90 |
| Comparative Example 2 | 50 | — | | 110 | 18 | 27 | 25 | 7 | 377 | 88 |
| Example 14 | 1000 | γ-alumina | 5.0 | 114 | 15 | 970 | 20 | 5 | 570 | 88 |
| Comparative Example 3 | 1000 | — | | 114 | 537 | 455 | 550 | 13 | 565 | 88 |
| Example 15 | 800 | γ-alumina | 3.0 | 108 | 10 | 770 | 15 | 5 | 230 | 93 |

Note:
$C_1 = C_2 - C_3$
$C_1$, $C_2$, and $C_3$ are based on the volume of the reaction product gas delivered from the reactor.

Table 2 clearly shows that when a carbonylation reaction of carbon monoxide with a nitrous acid ester in the presence of a solid catalyst and in the presence of a chlorine-containing substance (for example, hydrogen chloride) is carried out in the gas phase, and the resultant reaction product gas mixture containing, as a by-product or additive, a small amount of a chloroformic acid alkyl ester in addition to the targeted ester compound (for example, dimethyl carbonate or succinate) is subjected to the catalytic decomposition step of the present invention, the chloroformic acid alkyl ester can be decomposed and converted to the corresponding alkyl chloride, for example, methyl chloride at a high conversion, and simultaneously the content ($C_1$) by volume of hydrogen chloride contained in the reaction product-containing mixed gas is significantly reduced. Accordingly, the resultant product mixture can be refined without corroding the refining apparatus.

What we claim is:

1. A method of producing an ester compound comprising:
   (A) catalytically reacting, in the gas phase, carbon monoxide with a reactant comprising a nitrous acid ester, in 2. The method as claimed in claim 1, wherein the activated carbon has a specific surface area of 10 $m^2$/g or more.

3. The method as claimed in claim 1, wherein the inorganic oxides are selected from the group consisting of alumina, silica-alumina, synthetic zeolites, natural zeolites, silica, titania and zirconia.

4. The method as claimed in claim 1, wherein the inorganic oxides have a specific surface area of 10 $m^2$/g or more.

5. The method as claimed in claim 1, wherein the inorganic oxides is γ-alumina having a specific surface area of 10 $m^2$/g or more.

6. The method as claimed in claim 1, wherein the decomposition solid catalyst for step (B) is activated carbon.

7. The method as claimed in claim 1, wherein the solid catalyst for step (B) is employed in an amount of 2 to 500% based on the volume amount of the carbonylation reaction catalyst for step (A).

8. The method as claimed in claim 1, wherein the catalytic contact of step (B) is carried out at a temperature of 20° C. to 150° C.

9. The process as claimed in claim 1, wherein the nitrous acid ester is selected from esters of nitrous acid with monohydric aliphatic alcohols having 1 to 4 carbon atoms.

10. The process as claimed in claim 1, wherein the carbonylation reaction catalyst is a solid catalyst comprising a catalytic component comprising at least one metal selected from the platinum metal group and a solid carrier component on which the catalytic component is born.

11. The process as claimed in claim 1, wherein the reactant consists of a nitrous acid ester and the resultant ester compound is a carbonic acid ester.

12. The process as claimed in claim 1, wherein the reactant consists of a nitrous acid ester and an olefin, and the resultant ester compound is a dicarboxylic acid diester.

13. The process as claimed in claim 1, wherein the reactant consists of a nitrous acid ester and ethylene, and the resultant ester compound is a succinic acid diester.

14. The method as claimed in claim 1, wherein the solid decomposition catalyst for step (B) contains a metal component comprising a platinum group metal in an amount which is insufficient to serve as a catalyst component of the carbonylation reaction catalyst.

15. The method as claimed in claim 1, wherein the solid decomposition catalyst for the step (B) contains a metal component comprising a platinum group metal to a level of less than 0.1% ;by weight based on the weight of the solid decomposition catalyst.

\* \* \* \* \*